US012329202B2

(12) United States Patent
Tan et al.

(10) Patent No.: US 12,329,202 B2
(45) Date of Patent: Jun. 17, 2025

(54) ELECTRONIC ATOMIZATION DEVICE

(71) Applicant: SHENZHEN SMOORE TECHNOLOGY LIMITED, Shenzhen (CN)

(72) Inventors: Junwei Tan, Guangdong (CN); Houlin Chen, Shenzhen (CN); Zhihua Wen, Shenzhen (CN); Xiaowei Ye, Shenzhen (CN)

(73) Assignee: SHENZHEN SMOORE TECHNOLOGY LIMITED, Shenzhen (CN)

(*) Notice: Subject to any disclaimer, the term of this patent is extended or adjusted under 35 U.S.C. 154(b) by 783 days.

(21) Appl. No.: 17/521,826

(22) Filed: Nov. 8, 2021

(65) Prior Publication Data
US 2022/0061387 A1      Mar. 3, 2022

Related U.S. Application Data

(63) Continuation of application No. PCT/CN2020/088383, filed on Apr. 30, 2020.

(30) Foreign Application Priority Data

May 14, 2019   (CN) .......................... 201910399517.5

(51) Int. Cl.
*A24F 40/46*   (2020.01)
*A24F 40/10*   (2020.01)
(Continued)

(52) U.S. Cl.
CPC .............. *A24F 40/46* (2020.01); *A24F 40/10* (2020.01); *A24F 40/48* (2020.01); *A61M 11/042* (2014.02)

(58) Field of Classification Search
CPC .......... A24F 40/10; A24F 40/46; A24F 40/48; A24F 40/485; A61M 11/042
(Continued)

(56) References Cited

U.S. PATENT DOCUMENTS 7,589,340 B2 *   9/2009   Danes ................. A01M 1/2077
                                                                    73/290 R
2016/0255877 A1   9/2016   Wu
(Continued)

FOREIGN PATENT DOCUMENTS

CN        201226774 Y       4/2009
CN        203538384 U       4/2014
(Continued)

OTHER PUBLICATIONS

English Translation of WO2018133000 (Year: 2018).*
(Continued)

*Primary Examiner* — Sang Y Paik
(74) *Attorney, Agent, or Firm* — Andrew C. Cheng

(57) ABSTRACT

The disclosure discloses an electronic atomization device, including a housing, and an atomization unit and a baking unit which are disposed in the housing. The atomization unit includes a first airflow passage configured for bringing out an atomizing gas, and the baking unit includes a baking cavity. The atomization unit and the baking unit are disposed side by side in a transverse direction of the housing, and the first airflow passage is communicated with the baking cavity to enable a mixture of a smoke with an atomizing gas. Through a combined use of the atomization unit and the baking unit, a comprehensive requirement of a user on taste and mouthfeel can be met. Further, the atomization unit and the baking unit are disposed side by side in the transverse direction of the housing, such that the electronic atomization device is more compact in overall structure.

18 Claims, 11 Drawing Sheets

(51) Int. Cl.
*A24F 40/48* (2020.01)
*A61M 11/04* (2006.01)
(58) Field of Classification Search
USPC .......................................................... 392/390
See application file for complete search history.

(56) References Cited

U.S. PATENT DOCUMENTS

| | | | | |
|---|---|---|---|---|
| 2018/0042299 | A1* | 2/2018 | Han | ........................ A24F 40/30 |
| 2018/0279678 | A1 | 10/2018 | Hepworth | |
| 2020/0229501 | A1* | 7/2020 | Han | ........................ H05B 3/20 |
| 2020/0245681 | A1 | 8/2020 | An | |

FOREIGN PATENT DOCUMENTS

| | | | |
|---|---|---|---|
| CN | 103919279 | A | 7/2014 |
| CN | 104287096 | A | 1/2015 |
| CN | 204907924 | U | 12/2015 |
| CN | 105455195 | A | 4/2016 |
| CN | 206197012 | U | 5/2017 |
| CN | 106880086 | A | 6/2017 |
| CN | 206482014 | U | 9/2017 |
| CN | 206994431 | U | 2/2018 |
| CN | 207444276 | U | 6/2018 |
| CN | 207444283 | U | 6/2018 |
| CN | 108323815 | A | 7/2018 |
| CN | 108420112 | A | 8/2018 |
| CN | 207733664 | U | 8/2018 |
| CN | 207836775 | U | 9/2018 |
| CN | 207912057 | U | 9/2018 |
| CN | 108618205 | A | 10/2018 |
| CN | 208318228 | U | 1/2019 |
| CN | 208403253 | U | 1/2019 |
| CN | 109480338 | A | 3/2019 |
| CN | 208581843 | U | 3/2019 |
| CN | 109730364 | A | 5/2019 |
| CN | 208837093 | U | 5/2019 |
| CN | 110115398 | A | 8/2019 |
| CN | 110944532 | A | 3/2020 |
| CN | 111148441 | A | 5/2020 |
| CN | 210492620 | U | 5/2020 |
| JP | 2018516564 | A | 6/2018 |
| JP | 2018533919 | A | 11/2018 |
| JP | 2019521663 | A | 8/2019 |
| JP | 2020527955 | A | 9/2020 |
| JP | 2021500040 | A | 1/2021 |
| JP | 2021518742 | A | 8/2021 |
| KR | 20150000420 | U | 1/2015 |
| RU | 103281 | U1 | 4/2011 |
| RU | 111765 | U1 | 12/2011 |
| WO | 2017206480 | A1 | 12/2017 |
| WO | 2018133000 | A1 | 7/2018 |
| WO | 2018170829 | A1 | 9/2018 |
| WO | 2019017654 | A2 | 1/2019 |
| WO | 2019036853 | A1 | 2/2019 |
| WO | 2019081571 | A1 | 5/2019 |
| WO | 2019088562 | A2 | 5/2019 |

OTHER PUBLICATIONS

International Search Report of PCT Patent Application No. PCT/CN2020/088383 issued on Jul. 29, 2020.
The extended European search report of EP application No. 20805069.0 issued on Jun. 3, 2022.
The office action of RU application No. 2021133075/03 issued on Jul. 11, 2022.
International Written Opinion of PCT Patent Application No. PCT/CN2020/088383 issued on Jul. 29, 2020.
The Grant Decision of RU application No. 2021133062/03(069519) issued on Dec. 1, 2022.
The Grant Decision of RU application No. 2021133075/03(069534) issued on Dec. 1, 2022.
The extended European search report of EP application No. 20806021.0 issued on Jun. 3, 2022.
The office action of RU application No. 2021133062/03 issued on Jul. 11, 2022.
The office action of CN application No. 201920689268.9 issued on Feb. 27, 2020.
PCT search report and written opinion of PCT application No. PCT/CN2020/088382 issued on Jul. 29, 2020.
The office action of JP application No. 2021-567856 issued on Feb. 21, 2023.
The office action of JP application No. 2021-567859 issued on Apr. 4, 2023.
Communication pursuant to Article 94(3) EPC of EP application No. 20805069.0 issued on Feb. 29, 2024.
Communication pursuant to Article 94(3) EPC of EP application No. 20806021.0 issued on Feb. 29, 2024.
The first office action of CN application No. 201910399517.5 issued on Dec. 19, 2023.
The search report of CN application No. 201910399517.5 issued on Dec. 19, 2023.
The Non-Final Office Action of U.S. Appl. No. 17/522,872 issued on Feb. 16, 2024.
The second office action of CN patent application No. 201910399517.5 issued on May 18, 2024.
The search report of CN application No. 201910399517.5 issued on May 18, 2024.
The Final Rejection of U.S. Appl. No. 17/522,872 issued on Aug. 6, 2024.
Decision to Grant of JP application No. 2021-567856 issued on Sep. 5, 2023.
Decision to Grant of JP application No. 2021-567859 issued on Sep. 5, 2023.
Notice of Allowance of CN patent application No. 201910399517.5 issued on Sep. 6, 2024.
Search report of CN patent application No. 201910399517.5 issued on Sep. 6, 2024.
Non-Final Rejection of U.S. Appl. No. 17/522,872 issued on Nov. 19, 2024.

* cited by examiner

ELECTRONIC ATOMIZATION DEVICE

TECHNICAL FIELD

The present disclosure relates to the field of atomization devices, in particular to an electronic atomization device.

BACKGROUND

Traditional smoking is carried out by lighting tobacco with an open flame, which burns to generate smoke for a smoker to suck. The smoke generated by the combusion of the tobacco usually contains thousands of harmful substances, and therefore, the traditional tobacco not only causes a serious respiratory disease to the smoker, but also easily brings a second-hand smoke hazard.

In order to solve the technical problem that traditional tobacco combustion produces relatively more harmful substances, technicians have developed atomized electronic cigarettes and electronic flue-cured cigarettes. However, the atomized electronic cigarette generates smoke by atomizing e-liquid for a smoker to suck, and the electronic atomized cigarette overcomes the foregoing drawbacks of the traditional cigarette and can satisfy the dependence of a consumer on tobacco to a certain extent. However, the e-liquid of the electronic cigarette is prepared by flavors and fragrances, which is not a real cigarette product, and can not be widely accepted by consumers because of its light smoke and lack of tobacco aroma. A low-temperature electronic flue-cured cigarette in a related art uses a low-temperature (about 100 degrees Celsius) non-combustion manner to heat tobacco, because of its low heating temperature, the harmful substances generated by heating are less, but the amount of smoke is significantly insufficient. If the tobacco is heated at a high temperature, the tobacco is easy to be blackened and carbonized, and the heat distribution is not uniform, so that the problem that part of the tobacco has been carbonized and another part of the tobacco is insufficient in temperature is easily caused; and thereby more harmful substances are generated. How to smoke the aroma of the tobacco and reduce the harmful substances to a relatively great extent has become: an urgent problem to be solved in the tobacco industry.

SUMMARY

The present disclosure provides an improved electronic atomization device to overcome the drawbacks existing in the foregoing technology.

In order to achieve the above object, the present disclosure provides an electronic atomization device; including a housing, and an atomization unit and a baking unit which are disposed in the housing, the atomization unit including a first airflow passage configured for bringing out an atomizing gas, and the baking unit including a baking cavity; wherein the atomization unit and the baking unit are disposed side by side in a transverse direction of the housing, and the first airflow passage is communicated with the baking cavity to enable a mixture of a smoke with an atomizing gas.

In some embodiments, the first airflow passage includes a first air inlet and a first air outlet, the baking cavity includes a second air inlet and a second air outlet, and the first air outlet is communicated with the second air inlet.

In some embodiments, the first air outlet is located at a side of the atomization unit adjacent to the baking unit, and the first air inlet is located at a side of the atomization unit away from the baking unit.

In some embodiments, the first airflow passage extends transversely in the atomization unit, and the baking cavity extends longitudinally in the baking unit.

In some embodiments, the electronic atomization device further includes a communication unit including a communication passage for communicating a first air outlet of the atomization unit with a second air inlet of the baking cavity.

In some embodiments, the housing includes a suction nozzle; the baking unit is tubular and is longitudinally disposed in the housing, a lower end of the baking unit is connected with the communication unit, and an upper end of the baking unit is connected with the suction nozzle.

In some embodiments, the communication unit includes a third air outlet located at a top portion thereof and a third air inlet located on a side surface thereof adjacent to one side of the atomization unit, and the third air inlet is communicated with the first air outlet, and the third air outlet is communicated with the second air inlet.

In that embodiment, the communication unit includes a front half portion and a rear half portion which are spliced to each other, a surface of the front half portion toward the rear half portion is provided with a first arcuate groove having a semicircular cross section, a surface of the rear half portion toward the front half portion is provided with a second arcuate groove with a semicircular cross section, and the third air outlet is communicated with an upper end of the second arcuate groove, the third air inlet is communicated with a lower end of the second arcuate groove; when the front half portion and the rear half portion are spliced, the first arcuate groove and the second arcuate groove are enclosed to define the arc-shaped communication passage.

In some embodiments, a top portion of the rear half portion is further provided with a groove, and the groove is sleeved on a bottom end of the baking unit, so that the communication passage is communicated with the baking cavity.

In some embodiments, the atomization unit is detachably disposed in the housing.

In some embodiments, the atomization unit includes a base, an atomizing assembly disposed on the base, and an atomizing shell coupled to the base; the atomizing shell defines a liquid storage cavity for receiving a liquid medium, and the liquid storage cavity is fluidly connected with the atomizing assembly; the atomizing assembly includes an atomizing surface, and the atomizing surface is communicated with the first airflow passage.

In some embodiments, an outer side of the atomizing shell includes a convex pushing portion, and the housing is provided with a notch for exposing the pushing portion.

In some embodiments, the base includes an air guide hole, one end of the air guide hole is communicated the first airflow passage, and another end of the air guide hole extends downwards to a bottom surface of the base.

In some embodiments, the electronic atomization device further includes an air switch unit arranged in the housing in an upside-down manner, and a second airflow passage for communicating the air switch unit with the first airflow passage is defined in the housing.

In some embodiments, the housing includes a bracket including a bracket; the second air flow passage includes an arc-shaped first air guide groove defined on a top surface of the partition wall, and the first air guide groove extends from a first end of the partition wall away from the air switch unit to a second end of the partition wall adjacent to the air switch unit.

In some embodiments, the partition wall further includes a second air guide groove communicating with the second end of the first air guide groove and extending longitudinally downward, and a third air guide groove communicating the second air guide groove with the air switch unit.

In some embodiments, a bottom of the second air guide groove is lower than an end portion of the third air guide groove connected with the second air guide groove.

In some embodiments, the housing includes a cover covering on a top portion of the partition wall to seal the first air guide groove; the cover is provided with a vent hole communicated with the first end of the first air guide groove, and the vent hole is communicated with the air guide hole of the atomization unit.

In some embodiments, the air switch unit includes a mounting seat and an air switch disposed in the mounting seat, the mounting seat includes a receiving cavity with an opening at the top; the air switch is arranged in the top opening in an upside-down manner, and a space is defined between a triggering surface on top of the air switch and a bottom of the receiving cavity; the mounting base further includes a communication pipe for communicating the space with the outside; and the communicating pipe is communicated with the second airflow passage in the housing.

In some embodiments, the electronic atomization device further includes a power supply unit, the housing further includes a suction nozzle, the power supply unit is disposed at a distal end of the housing away from the suction nozzle, and the atomization unit and the baking unit are disposed at a proximal end of the housing adjacent to the suction nozzle.

In some embodiments, the baking unit includes a tubular heating member, a tubular heat conducting member coaxially disposed in the heating member, and a tubular protecting member coaxially disposed outside the heating member.

The disclosure has the following beneficial effects: through a combined use of the atomization unit and the baking unit, a comprehensive requirement of a user on taste and mouthfeel can be met. Further, the atomization unit and the baking unit are disposed side by side in the transverse direction of the housing, so that the electronic atomization device is more compact in overall structure.

PREFERRED EMBODIMENTS

In order to more clearly understand the present disclosure, the present disclosure will now be described in detail with reference to the accompanying drawings.

Figure 1:
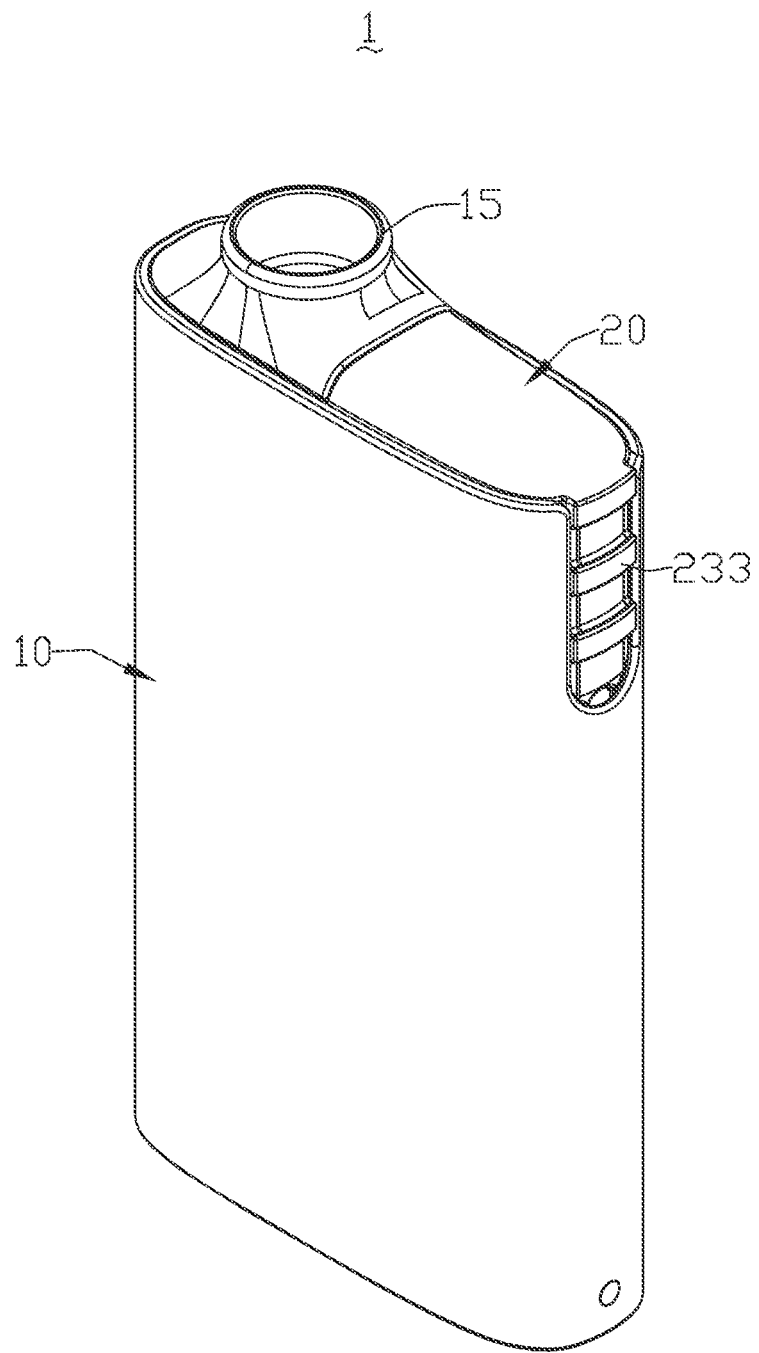
FIG. 1 is a schematic perspective view of an electronic atomization device according to some embodiments of the present disclosure.
Figure 2:
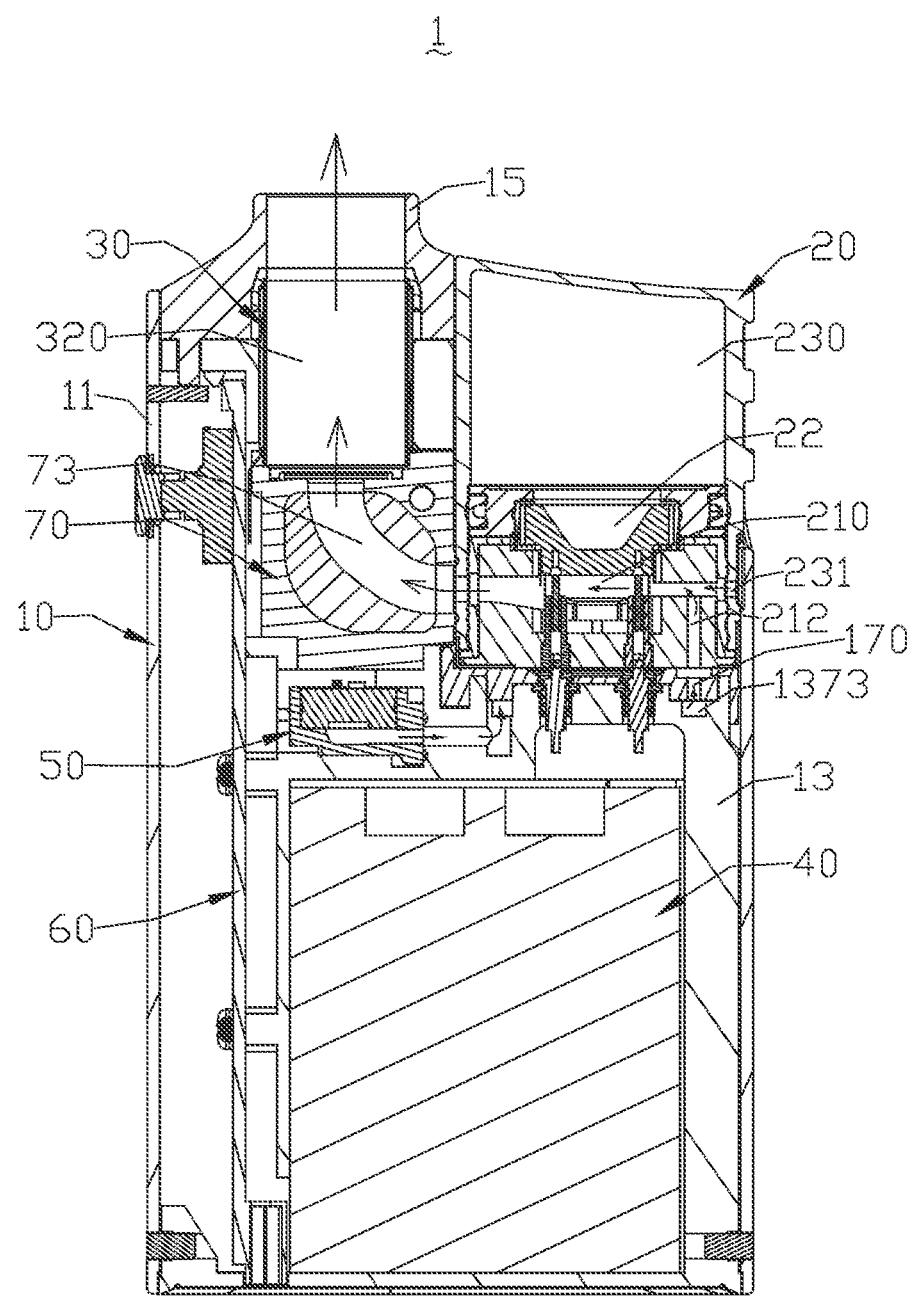
FIG. 2 is a longitudinal sectional view of the electronic atomization device shown in FIG. 1.
Figure 3:
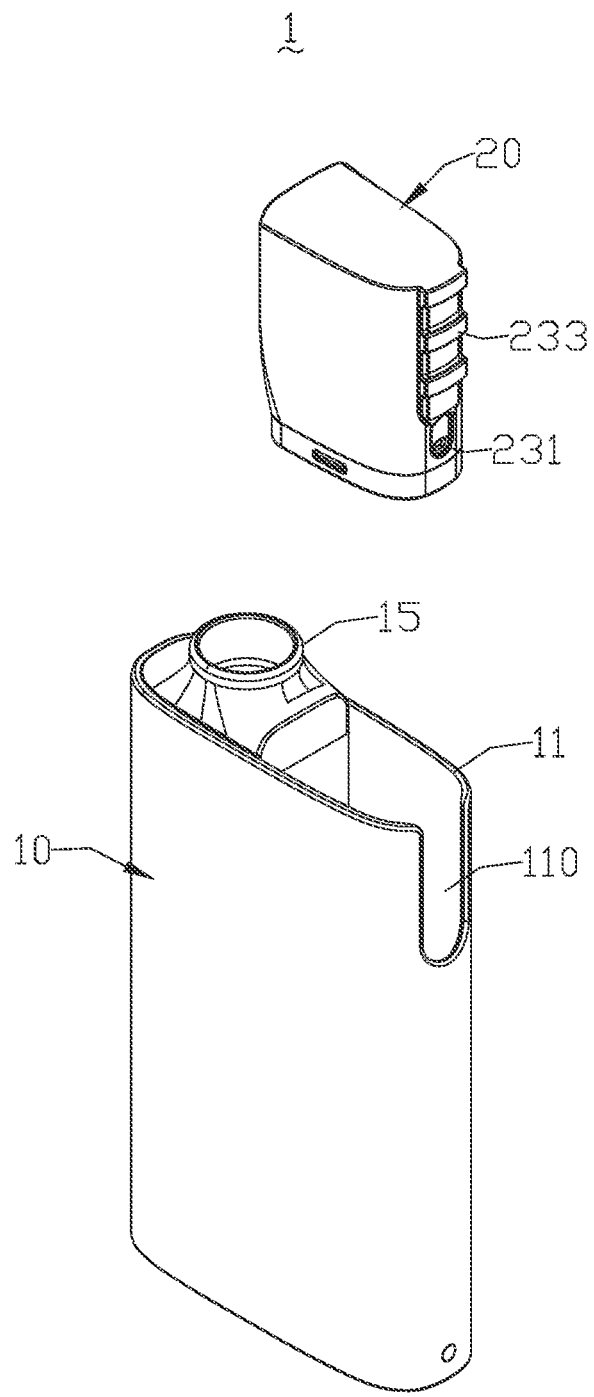
FIG. 3 is a partially exploded perspective view of the electronic atomization device shown in FIG. 1.
Figure 4:
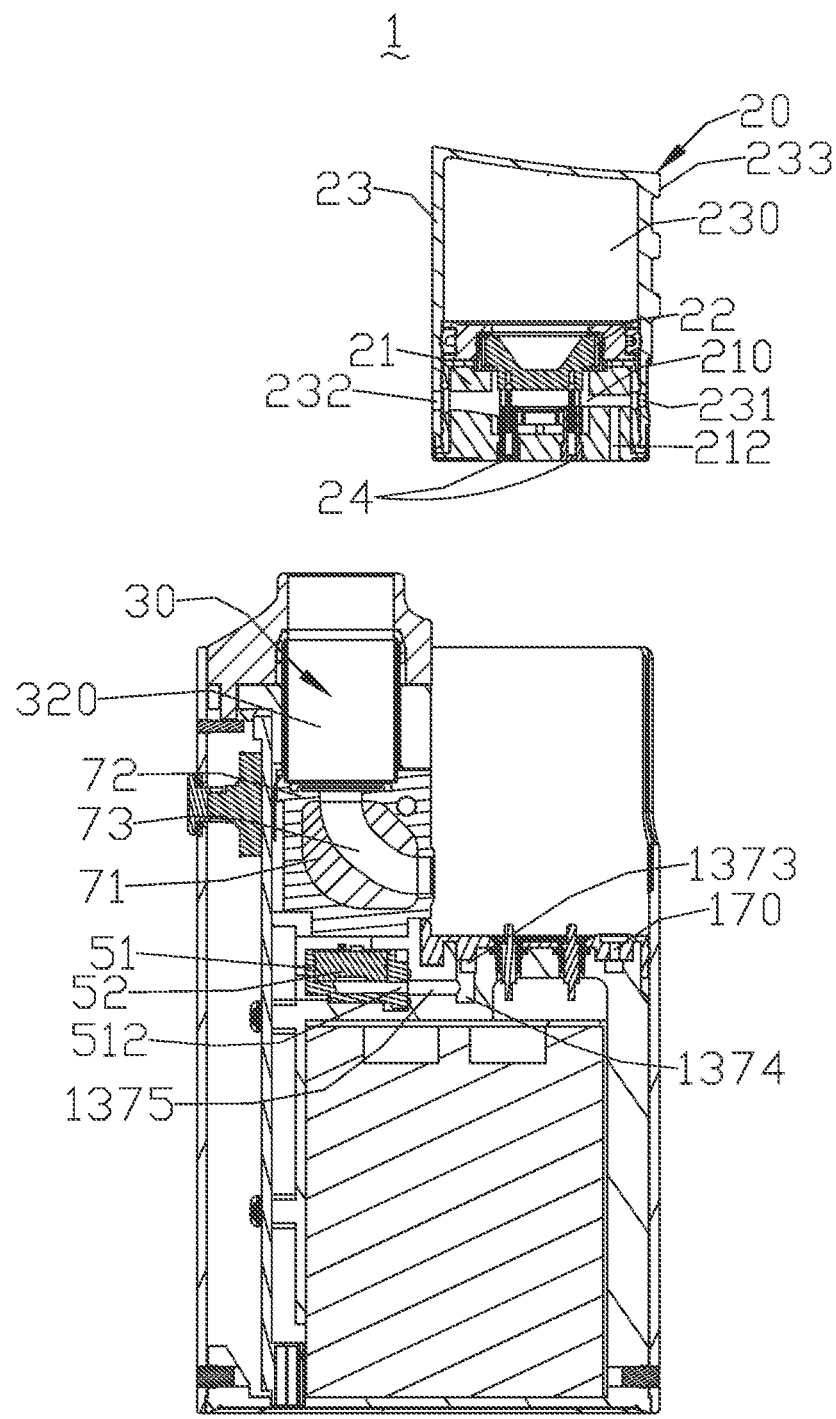
FIG. 4 is a longitudinal sectional view of the electronic atomization device shown in FIG. 3 in an exploded state.

FIG. 1 and FIG. 2 show an electronic atomization device 1 in some embodiments of the present disclosure, the electronic atomization device 1 may include a housing 10, and an atomization unit 20, a baking unit 30, a power supply unit 40, an air switch unit 50, a main control unit 60 and a communication unit 70 which are disposed in the housing 10. The atomization unit 20 is configured to atomize a liquid medium such as an e-liquid or the like, and the baking unit 30 is configured to heat a solid smoke generating medium 2 such as a flavor bomb or the like to generate smoke. The atomization unit 20 and the baking unit 30 are disposed in an upper portion of the housing 10 side by side, that is, disposed in the upper portion of housing 10 in a transverse direction thereof. The power supply unit 40 is configured to supply power to the atomization unit 20 and the baking unit 30, and is disposed in a lower portion of the housing 10, that is, the power supply unit 40 and the atomization unit 20 and the baking unit 30 are distributed in a longitudinal direction of the housing 10. The air switch unit 50 is disposed between the baking unit 30 and the power supply unit 40, and is configured for controlling the on-off between the power supply unit 40 and the atomization unit 20 and the baking unit 30 through a driving of an airflow. The main control unit 60 is disposed in a side portion of the housing 10, and is configured to implement functions such as unlocking, data input, control and the like of the electronic atomization device 1. The communication unit 70 is disposed at a lower portion of the baking unit 30, and is configured to communicate the baking unit 30 with the atomization unit 20, so that the smoke and the atomizing gas can be mixed and then be transferred out, thereby meeting a user's requirement. Referring to FIG. 3 and FIG. 4, the atomization unit 20 in some embodiments is removably disposed in the housing 10, so that replacement of the atomization unit 20 is enabled. The power supply unit 40 includes a battery.

Figure 5:
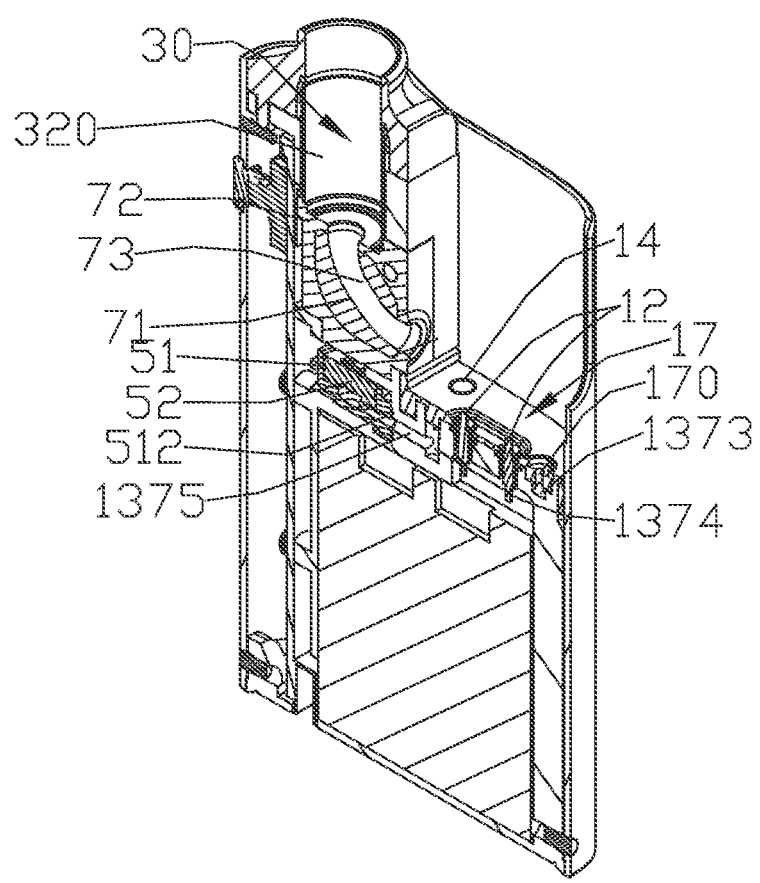
FIG. 5 is a longitudinal sectional view of the electronic atomization device shown in FIG. 1 when an atomization unit is removed.
Figure 6:
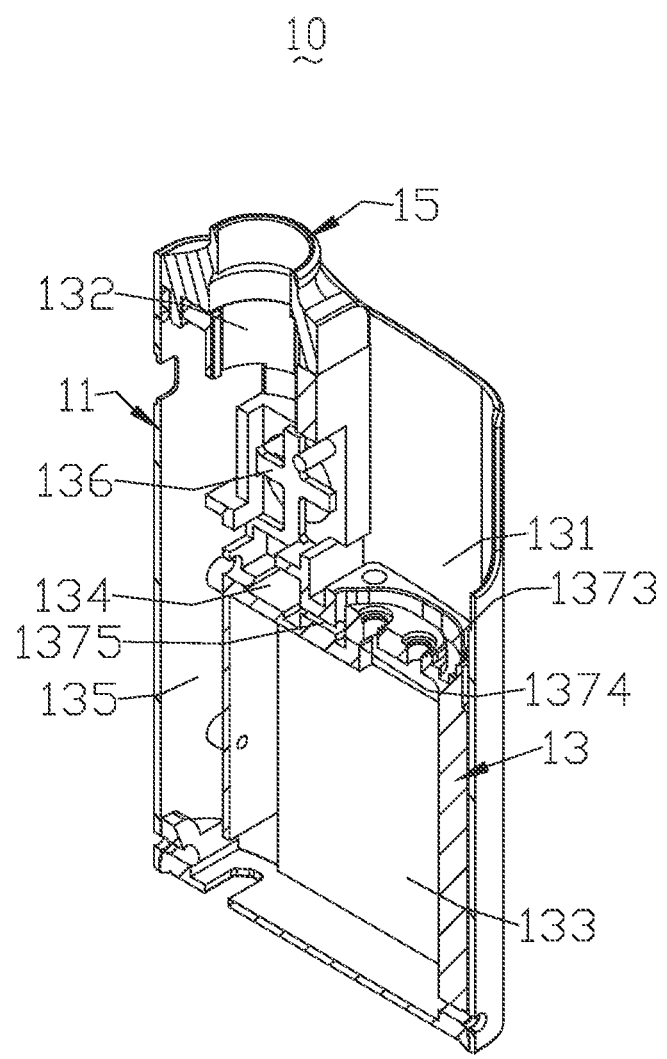
FIG. 6 is a schematic perspective sectional view of a housing of the electronic atomization device shown in FIG. 1.
Figure 7:
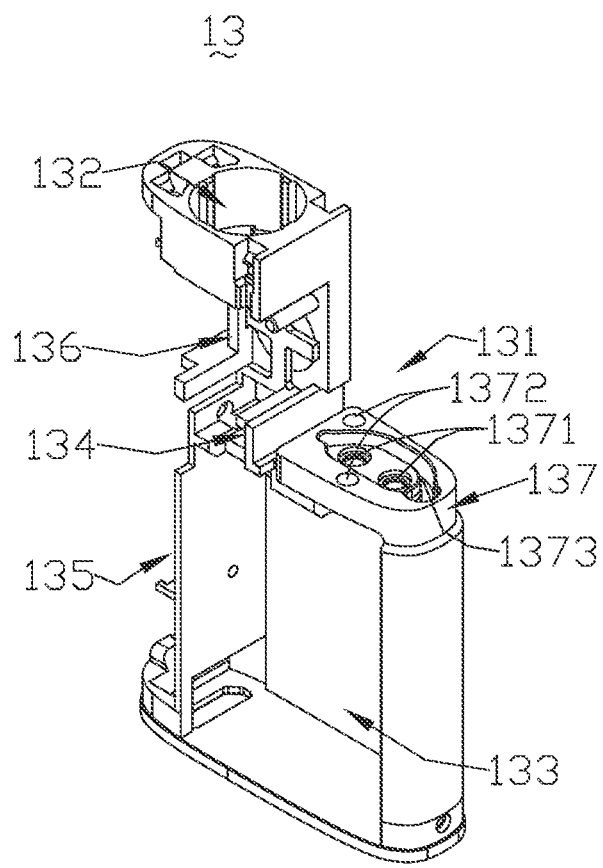
FIG. 7 is a schematic perspective view of a bracket of the electronic atomization device shown in FIG. 1.

Referring to FIG. 5 and FIG. 6, the housing 10 in some embodiments may be in an elongated and flat shape, and may include a sleeve 11, a bracket 13 disposed in the sleeve 11, and a suction nozzle 15 disposed on a top end of the bracket 13. The bracket 13 may be integrally formed in some embodiments, and may include a first receiving space 131 for receiving the atomization unit 20, a second receiving space 132 for receiving the baking unit 30, a third receiving space 133 for receiving the power supply unit 40, a fourth receiving space 134 for receiving the air switch unit 50, a fifth receiving space 135 for receiving the main control unit 60, and a sixth receiving space 136 for receiving the communication unit 70. A partition wall 137 is provided between the first receiving space 131 and the third receiving space 133, and a top surface of the partition wall 137 is provided with a pair of electrode holes 1371, a pair of magnetic member receiving holes 1372, and an arc-shaped first air guide groove 1373, The pair of electrode holes 1371 are spaced disposed in a length direction of the partition wall 137. The first air guide groove 1373 extends from a first end away from the fourth receiving space 134 to a second end adjacent to the fourth receiving space 134. The third receiving space 133 is located at a distal end away from the the suction nozzle 15, and the first receiving space 131 and the second receiving space 132 are located at a proximal end adjacent to the suction nozzle 15. Correspondingly, the power supply unit 40 is located at the distal end away from the suction nozzle 15, and the atomization unit 20 and the baking unit 30 are located at the proximal end adjacent to the suction nozzle 15, so that the electronic atomization device 1 is more compact in overall structure.

As further shown in FIG. 6, the partition wall 137 further includes a second air guide groove 1374 communicating with the second end of the first air guide groove 1373 and extending longitudinally downward, and a third air guide groove 1375 communicating the second air guide groove 1374 with the fourth receiving space 134 and extending transversely, so as to define a second airflow passage communicating with the air switch unit 50. The first air guide groove 1373 is in an arc shape, so that the possibility that the leakage liquid enters the air switch unit 50 can be reduced to a certain extent, so as to prevent the leakage liquid from adversely affecting the air switch unit 50. Preferably, a bottom of the second air guide groove 1374 is lower than an end portion of the third air guide groove 1375 connected with the second air guide groove 1374, thus even if the leakage liquid enters the second airflow passage, a lower end of the second air guide groove 1374 is able to receive some of the leakage liquid, so as to further reduce the possibility of the leakage liquid entering the air switch unit 50.

As further shown in FIG. 4, in some embodiments, the atomization unit 20 may include a base 21, an atomizing assembly 22 disposed on the base 21, and an atomizing shell 23 sleeved on the base 21. The atomizing shell 23 defines a liquid storage cavity 230 for receiving the liquid medium. A liquid absorbing surface on top of the atomizing assembly 22 is exposed in the liquid storage cavity 230 so as to be fluidly connected with the liquid storage cavity 230. The base 21 includes a first airflow passage 210 extending laterally and located below the atomizing assembly 22, and an atomizing surface on bottom of the atomizing assembly 22 is exposed in the first airflow passage 210, An outer side and an inner side of the atomizing shell 23 are respectively provided with an air inlet 231 and an air outlet 232 communicated with the first airflow passage 210. The air inlet 231 allows external air to enter the first airflow passage 210 to be mixed with the atomizing gas generated by the atomizing assembly 22, The air outlet 232 allows the mixed gas to flow out of the atomization unit 20. An outer side of the atomizing shell 23 is further provided with a plurality of convex pushing portions 233 to facilitate pushing the atomization unit 20 out of the housing 10. Correspondingly, the sleeve 11 of the housing 10 is provided with a notch 110 for exposing the pushing portions 233. In some embodiments, the base 21 may further include an air guide hole 212, one end of the air guide hole 212 is communicated with an end of the first airflow passage 210 adjacent to the air inlet 231, and another end of the air guide hole 212 extends downward to a bottom surface of the base 21 for communicating with the second airflow passage in the bracket 13. The atomization unit 20 may further include a pair of electrodes 24 extending through a bottom surface of the base 21 and electrically connected to the atomizing assembly 22.

As further shown in FIG. 5, the housing 10 in some embodiments further includes a cover 17, a pair of electrode contacts 12, and a pair of magnetic members 14. The cover 17 covers a top of the partition wall 137 to seal the first air guide groove 1373. The electrode contact 12 extends through the electrode hole 1371 and is electrically connected to the power supply unit 40. The magnetic member 14 is embedded in the magnet receiving hole 1372 to adsorb the atomization unit 20, The cover 17 defines a vent hole 170 communicating with the first end of the first air guide groove 1373. The vent hole 170 is configured to communicate the second airflow passage with the air guide hole 212 of the atomization unit 20. The cover 17 is further provided with an opening (not numbered) for exposing the electrode contacts 12 and the magnetic members 14.

Figure 8:
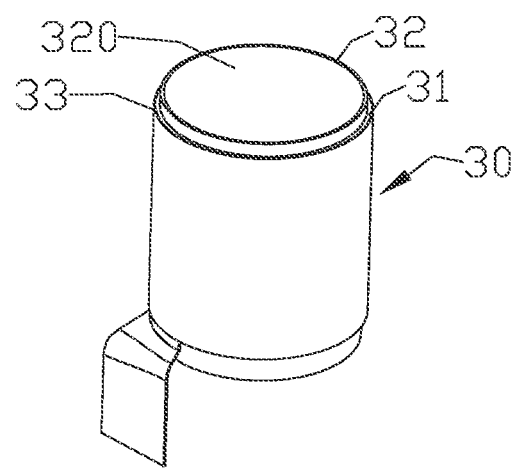
FIG. 8 is a schematic perspective view of a baking unit of the electronic atomization device shown in FIG. 1.
Figure 9:
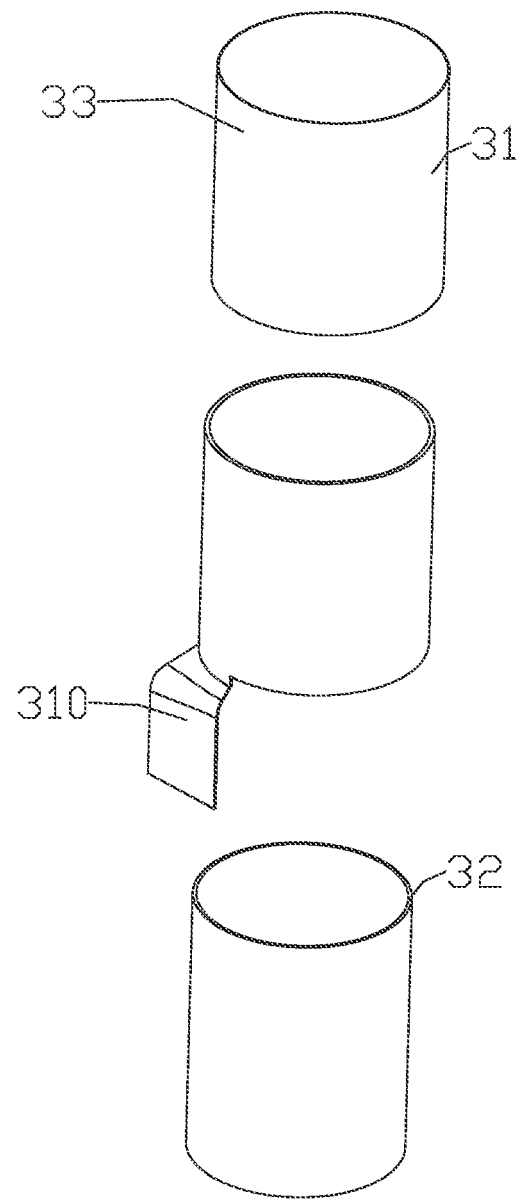
FIG. 9 is an exploded perspective view of the baking unit shown in FIG. 8.

As shown in FIG. 8 and FIG. 9, the Taking unit 30 may be in a tubular shape in some embodiments, and is longitudinally disposed in the housing 10. A lower end of the the baking unit 30 is connected to the communication unit 70, and an upper end of the the baking unit 30 is connected to the suction nozzle 15. In some embodiments, the baking unit 30 may include a tubular heating member 31, a tubular heat conducting member 32 coaxially disposed in the heating member 31, and a tubular protecting member 33 coaxially disposed outside the heating member. The heating member 31 may include an electrode lead 310, The tubular heat conducting member 32 defines a baking cavity 320 for receiving the solid smoke generating medium 2, and the baking cavity 320 has an air inlet at a bottom end and an air outlet at a top end. The tubular heat conducting member 32 can be made of a material with good thermal conductivity, such as copper, aluminum, stainless steel or the like, and is electrically insulated from the heating member 31 to isolate the heating member 31 from the solid smoke generating medium, so as to prevent the heating member 31 from being damaged due to external contamination. The tubular protecting member 33 may be made of an electrically insulating material, and is coated on an outer periphery of the heating member to protect the heating member from a fault such as a short circuit. The baking unit 30 can heat the solid smoke generating medium such as tobacco or the like in a low-temperature non-combustible manner, so that can generate fewer harmful substances when heating due to the low heating temperature. Preferably, the heating temperature of the baking unit 30 is a temperature that maintains an internal temperature of the solid smoke generating medium at 40 to 50 degrees. In some embodiments, the heating temperature of the baking unit 30 is 45 to 55 degrees.

Figure 10:
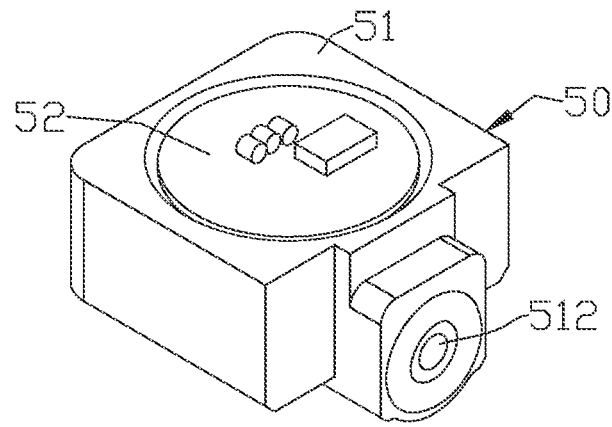
FIG. 10 is a schematic perspective view of an air switch unit of the electronic atomization device shown in FIG. 1.
Figure 11:
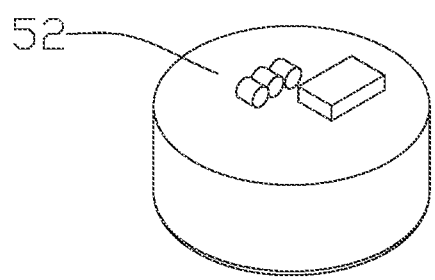
FIG. 11 is an exploded perspective view of the air switch unit shown in FIG. 10.
Figure 11:
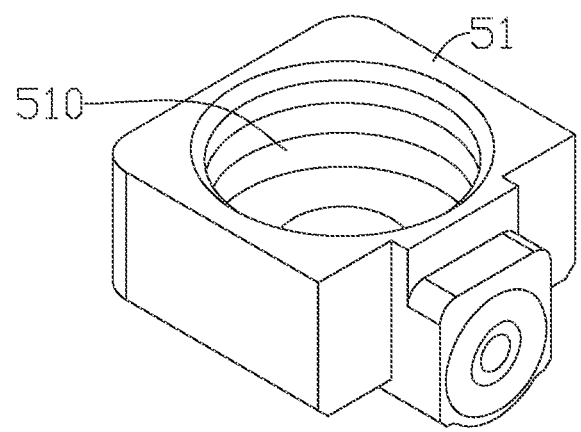

As shown in FIG. 10 and FIG. 11, in some embodiments, the air switch unit 50 may include a mounting seat 51 and an air switch 52 disposed in the mounting seat 51. The mounting seat 51 includes a receiving cavity 510 with an opening at the top. As shown in FIG. 4 and FIG. 5, the air switch 52 is arranged in the top opening in an upside-down manner, and a space is defined between a triggering surface on top of the air switch 52 and a bottom of the receiving cavity 510. The mounting base 51 further includes a communicating pipe 512 for communicating the space with the outside. The communicating pipe 512 is configured to be communicated with the second airflow passage in the housing 10, Thus, the triggering surface of the air switch 52 is communicated with the first airflow passage 210 of the atomization unit 20 via the second airflow passage. When the first airflow passage 210 has an airflow suckion, a negative pressure will be formed in the second airflow passage, and further, a negative pressure is formed at the triggering surface of the air switch 52 to turn on the air switches 52. It should be noted that, since the air switch 52 is arranged in the upside-down manner, and the space is defined between the air switch 52 and the bottom of the receiving cavity 510, so that even if the leakage liquid enters the receiving cavity 510, it will not touch the triggering surface of the air switch 52 easily, thereby further ensuring the normal operation of the air switch 52.

Figure 12:
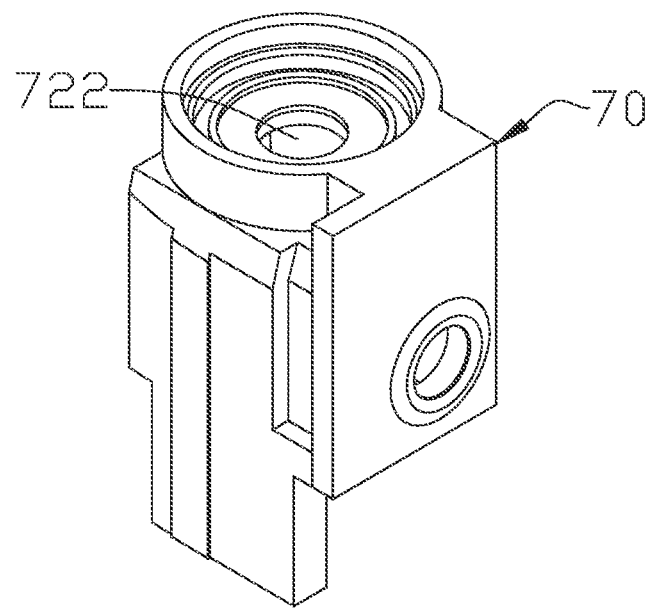
FIG. 12 is a schematic perspective view of a communication unit of the electronic atomization device shown in FIG. 1.
Figure 13:
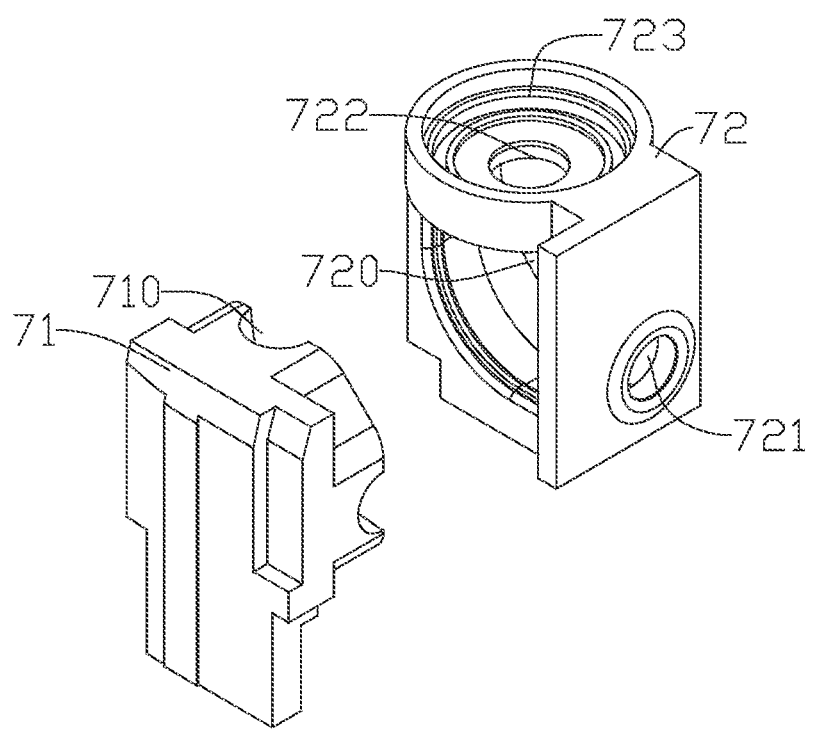
FIG. 13 is an exploded perspective view of the communication unit shown in FIG. 12.

As shown in FIG. 12 and FIG. 13, the communication unit 70 in some embodiments may include a front half portion 71 and a rear half portion 72 which are spliced to each other. A surface of the front half portion 71 toward the rear half portion 72 is provided with a first arcuate groove 710 having a semicircular cross section. A surface of the rear half portion 72 toward the front half portion 71 is provided with a second arcuate groove 720 with a semicircular cross section, and a top portion of the rear half portion 72 is further provided with an air outlet 722 communicating with an upper end of the second arcuate groove 720, and a side of the rear half portion 72 adjacent to the atomization unit 20 is provided with an air inlet 721 communicating with a lower end of the second arcuate groove 720. The front half portion 71 and the rear half portion 72 are joined to define an arcuate communication passage 73 for guiding a transverse airflow to a longitudinal airflow.

Further, as shown in FIG. 2, the communication passage 73 communicates the first airflow passage 210 extending transversely of the atomization unit 20 with the baking chamber extending longitudinally of the baking unit 30. A top portion of the rear half portion 72 is further provided with a circular groove 723 which is tightly sleeved on a bottom of the baking unit 30 so as to enable the communication passage 73 to be tightly communicated with the baking cavity of the baking unit 30.

Figure 14:
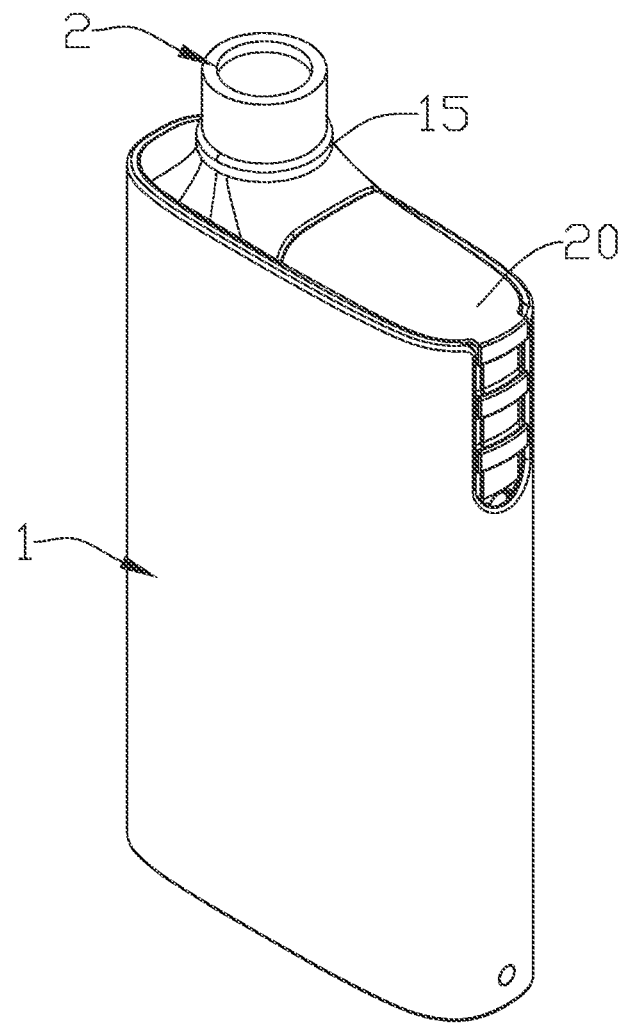
FIG. 14 is a schematic perspective view of the electronic atomization device of FIG. 1 when a solid smoke generating medium is inserted.

Referring to FIG. 14, the following steps can be adopted during a use process of the electronic atomization device 1:
(1) The atomization unit 20 with the liquid medium (not shown) is inserted into the housing 10, with the electrodes 24 of the atomization unit 20 electrically contacting with the electrode contacts 12 on the housing 10.
(2) The solid smoke generating medium 2 is inserted into the baking unit 30 via the suction nozzle 15.
(3) Sucking via the suction nozzle 15, the airflow drives the air switch 52 to be turned on, and the atomization unit 20 starts to atomize the liquid medium to generate the atomizing gas, and the baking unit 30 starts to bake the solid smoke generating medium 2 to generate the smoke.
(4) Finally, the mixture of the air with the atomizing gas and the smoke flows out of the electronic atomization device 1 via the suction nozzle 15.

It can be understood that the baking unit 30 can be used to atomize the liquid medium to generate the atomizing gas when the solid smoke generating medium 2 is not needed to be baked.

The above embodiments are only preferred embodiments of the disclosure, but the disclosure is not limited thereto, and any variations that a person skilled in the art can think of should fall within the scope of protection of the present disclosure.

What is claimed is:

1. An electronic atomization device, comprising a housing, and an atomization unit and a baking unit which are disposed in the housing, the atomization unit comprising a first airflow passage configured for bringing out an atomizing gas, and the baking unit comprising a baking cavity; wherein the atomization unit and the baking unit are disposed side by side in a transverse direction of the housing, and the first airflow passage is communicated with the baking cavity to enable a mixture of a smoke with an atomizing gas;
wherein the electronic atomization device further comprises an air switch unit arranged under the baking unit, the air switch unit comprises a mounting seat and an air switch, the mounting seat comprises a receiving cavity with a top opening facing a bottom of the baking unit, the air switch is arranged in the top opening of the receiving cavity, a space is defined between a triggering surface of the air switch and a bottom of the receiving cavity, and a second airflow passage for communicating the triggering surface of the air switch unit with the first airflow passage is defined in the housing.

2. The electronic atomization device according to claim 1, wherein the first airflow passage comprises a first air inlet and a first air outlet, the baking cavity comprises a second air inlet and a second air outlet, and the first air outlet is communicated with the second air inlet.

3. The electronic atomization device according to claim 2, wherein the first air outlet is located at a side of the atomization unit adjacent to the baking unit, and the first air inlet is located at a side of the atomization unit away from the baking unit.

4. The electronic atomization device according to claim 1, wherein the first airflow passage extends transversely in the atomization unit, and the baking cavity extends longitudinally in the baking unit.

5. The electronic atomization device according to claim 4, wherein the electronic atomization device further comprises a communication unit comprising a communication passage for communicating a first air outlet of the atomization unit with a second air inlet of the baking cavity.

6. The electronic atomization device of claim 5, wherein the housing comprises a suction nozzle; the baking unit is tubular and is longitudinally disposed in the housing, a lower end of the baking unit is connected with the communication unit, and an upper end of the baking unit is connected with the suction nozzle.

7. The electronic atomization device according to claim 5, wherein the communication unit comprises a third air outlet located at a top portion thereof and a third air inlet located on a side surface thereof adjacent to one side of the atomization unit, and the third air inlet is communicated with the first air outlet, and the third air outlet is communicated with the second air inlet.

8. The electronic atomization device according to claim 1, wherein the atomization unit comprises a base, an atomizing assembly disposed on the base, and an atomizing shell coupled to the base; the atomizing shell defines a liquid storage cavity for receiving a liquid medium, and the liquid storage cavity is fluidly connected with the atomizing assembly; the atomizing assembly comprises an atomizing surface, and the atomizing surface is communicated with the first airflow passage; wherein an outer side of the atomizing shell comprises a convex pushing portion, and the housing is provided with a notch for exposing the pushing portion.

9. The electronic atomization device according to claim 8, wherein the base comprises an air guide hole, one end of the air guide hole is communicated with the first airflow passage, and another end of the air guide hole extends downwards to a bottom surface of the base.

10. The electronic atomization device of claim 1, wherein the mounting seat further comprises a communication pipe for communicating the space with outside; and the communicating pipe is communicated with the second airflow passage in the housing.

11. The electronic atomization device according to claim 1, wherein the electronic atomization device further comprises a power supply unit, the housing further comprises a suction nozzle, the power supply unit is disposed at a distal end of the housing away from the suction nozzle, and the atomization unit and the baking unit are disposed at a proximal end of the housing adjacent to the suction nozzle.

12. The electronic atomization device according to claim 1, wherein the baking unit comprises a tubular heating member, a tubular heat conducting member coaxially disposed in the heating member, and a tubular protecting member coaxially disposed outside the heating member.

13. An electronic atomization device, comprising a housing, and an atomization unit and a baking unit which are disposed in the housing, the atomization unit comprising a first airflow passage configured for bringing out an atomizing gas, and the baking unit comprising a baking cavity; wherein the atomization unit and the baking unit are disposed side by side in a transverse direction of the housing, and the first airflow passage is communicated with the baking cavity to enable a mixture of a smoke with an atomizing gas;

wherein the electronic atomization device further comprises a communication unit comprising a communication passage for communicating a first air outlet of the atomization unit with a second air inlet of the baking cavity;

wherein the communication unit comprises a third air outlet located at a top portion thereof and a third air inlet located on a side surface thereof adjacent to one side of the atomization unit, and the third air inlet is communicated with the first air outlet, and the third air outlet is communicated with the second air inlet; and wherein the communication unit comprises a front half portion and a rear half portion which are spliced to each other, a surface of the front half portion toward the rear half portion is provided with a first arcuate groove having a semicircular cross section, a surface of the rear half portion toward the front half portion is provided with a second arcuate groove with a semicircular cross section, and the third air outlet is communicated with an upper end of the second arcuate groove, the third air inlet is communicated with a lower end of the second arcuate groove; when the front half portion and the rear half portion are spliced, the first arcuate groove and the second arcuate groove are joined to define the arc-shaped communication passage.

14. The electronic atomization device according to claim 13, wherein a top portion of the rear half portion is further provided with a groove, and the groove is sleeved on a bottom end of the baking unit, so that the communication passage is communicated with the baking cavity.

15. An electronic atomization device, comprising a housing, and an atomization unit and a baking unit which are disposed in the housing, the atomization unit comprising a first airflow passage configured for bringing out an atomizing gas, and the baking unit comprising a baking cavity;

wherein the atomization unit and the baking unit are disposed side by side in a transverse direction of the housing, and the first airflow passage is communicated with the baking cavity to enable a mixture of a smoke with an atomizing gas;

wherein the electronic atomization device further comprises an air switch unit arranged in the housing, and a second airflow passage for communicating the air switch unit with the first airflow passage is defined in the housing; and wherein the housing comprises a bracket; the second air flow passage comprises an arc-shaped first air guide groove defined on a top surface of a partition wall, and the first air guide groove extends from a first end of the partition wall away from the air switch unit to a second end of the partition wall adjacent to the air switch unit.

16. The electronic atomization device according to claim 15, wherein the partition wall further comprises a second air guide groove communicating with the second end of the first air guide groove and extending longitudinally downward, and a third air guide groove communicating the second air guide groove with the air switch unit.

17. The electronic atomization device according to claim 16, wherein a bottom of the second air guide groove is lower than an end portion of the third air guide groove connected with the second air guide groove.

18. The electronic atomization device according to claim 15, wherein the housing comprises a cover covering on a top portion of the partition wall to seal the first air guide groove; the cover is provided with a vent hole communicated with the first end of the first air guide groove, and the vent hole is communicated with the air guide hole of the atomization unit.

* * * * *